Figure 1:
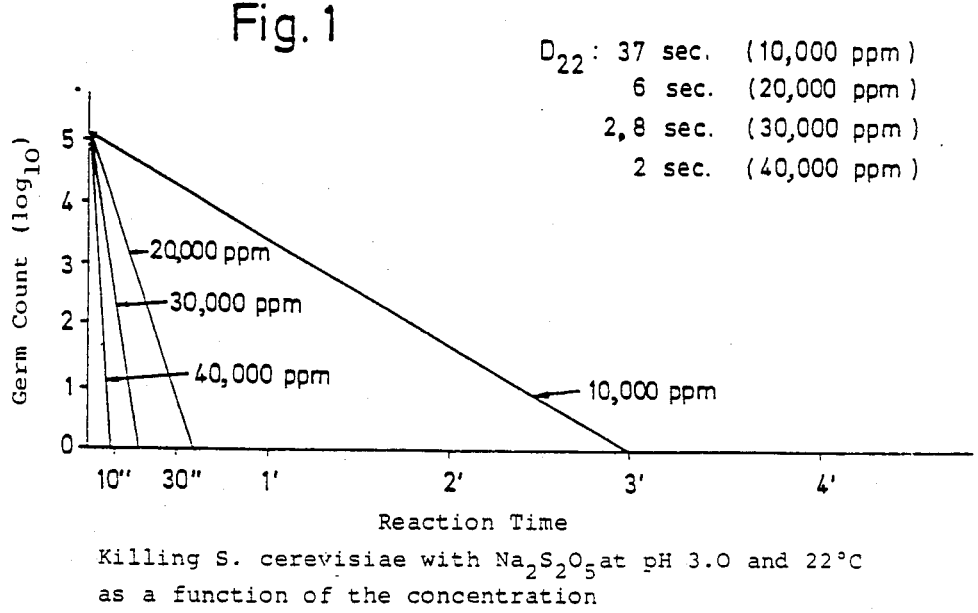

United States Patent [19]

Wartenberg et al.

[11] Patent Number: 4,732,735
[45] Date of Patent: Mar. 22, 1988

[54] METHOD OF STERILIZING PACKING MATERIALS FOR THE ASEPTIC PACKAGING OF FRUIT JUICE AND WINE

[75] Inventors: Erwin W. Wartenberg, Stuttgart; Hong-An Duong, Filderstadt, both of Fed. Rep. of Germany

[73] Assignee: Tetra Pak Developpement S.A., Pully, Switzerland

[21] Appl. No.: 33,021

[22] Filed: Mar. 31, 1987

Related U.S. Application Data

[63] Continuation of Ser. No. 745,337, Jun. 17, 1985, abandoned.

[51] Int. Cl.⁴ .......................... A23C 3/00; B65B 55/04
[52] U.S. Cl. .................................. 422/28; 422/27; 424/162; 424/164; 426/407; 426/392; 426/399; 426/521; 53/425; 53/426

[58] Field of Search ................... 422/27, 28; 424/162, 424/164; 426/407, 392, 521, 399–401; 53/425, 426, 167

[56] References Cited

U.S. PATENT DOCUMENTS

| | | | |
|---|---|---|---|
| 3,180,740 | 4/1965 | Martin | 422/27 X |
| 3,440,319 | 4/1969 | Wilson | 424/130 X |
| 4,404,040 | 9/1983 | Wang | 422/28 X |
| 4,500,517 | 2/1985 | Luss | 424/162 |

Primary Examiner—Barry S. Richman
Assistant Examiner—Lynn M. Kummert
Attorney, Agent, or Firm—Neuman, Williams, Anderson & Olson

[57] ABSTRACT

When sterilizing packing materials for the aseptic packaging of fruit juice and wine using sulfurous acid it is suggested that the packing material be treated with an aqueous solution of sulfurous acid and alcohol.

13 Claims, 24 Drawing Figures

Synergistic effect of $Na_2S_2O_5$ (10,000 ppm/pH 3.0) and alcohol 15 % when killing S. cerevisiae (temperature 22°C)

Killing S. cerevisiae with $Na_2S_2O_5$ at pH 3.0 and 22°C as a function of the concentration Killing Saccharomyces cerevisiae with $Na_2S_2O_5$ (10,000 ppm, pH 3) as a function of the temperature Synergistic effect of $Na_2S_2O_5$ (10,000 ppm/pH 3.0) and alcohol 15 % when killing S. cerevisiae (temperature 22°C)

Killing A. niger with $Na_2S_2O_5$ at pH 3 as a function of the concentration and the temperature Killing A. niger with $Na_2S_2O_5$ (10,000 ppm, pH 3) and Alcohol (15 %) at 22°C Killing Mucor with $Na_2S_2O_5$, pH 3.0 at 22°C as a function of the concentration Killing Mucor with Na$_2$S$_2$O$_5$ (10,000 ppm, pH 3.0) as a function of the temperature Killing Mucor with Na$_2$S$_2$O$_5$ (10,000 ppm, pH 3) and Ethanol (10 %) at 22°C Killing Mucor with $Na_2S_2O_5$ (10,000 ppm, pH 3) and Ethanol (10 %) at 50°C Killing Gluconobacter with $Na_2S_2O_5$ (pH 3) at 22°C as a function of the concentration Killing Gluconobacter with $Na_2S_2O_5$ (10,000 ppm and 40,000 ppm, pH 3) as a function of the temperature Killing Acetobacters (Gluconobacter) with $Na_2S_2O_5$ (30,000 ppm, pH 3.0) and Alcohol (30 %) at 22°C Killing Acetobacters (Gluconobacter) with Na$_2$S$_2$O$_5$ (20,000 ppm, pH 3) and Alcohol (15 %) at 50°C Killing Acetobacters (A. aceti) with Na$_2$S$_2$O$_5$ (20,000 ppm, pH 3) and Alcohol (15 %) at 50°C Killing Leuconostoc dextranicum with $Na_2S_2O_5$ (10,000 ppm/pH 3) as a function of the temperature Killing Leuconostoc dextranicum with $Na_2S_2O_5$ (20,000 ppm, pH 3) and Ethanol (15 %) at 22°C Synergistic effect of $Na_2S_2O_5$ (10,000 ppm / pH 3.0) and 2-Butanol (5 %) at 22°C for killing S. cerevisiae

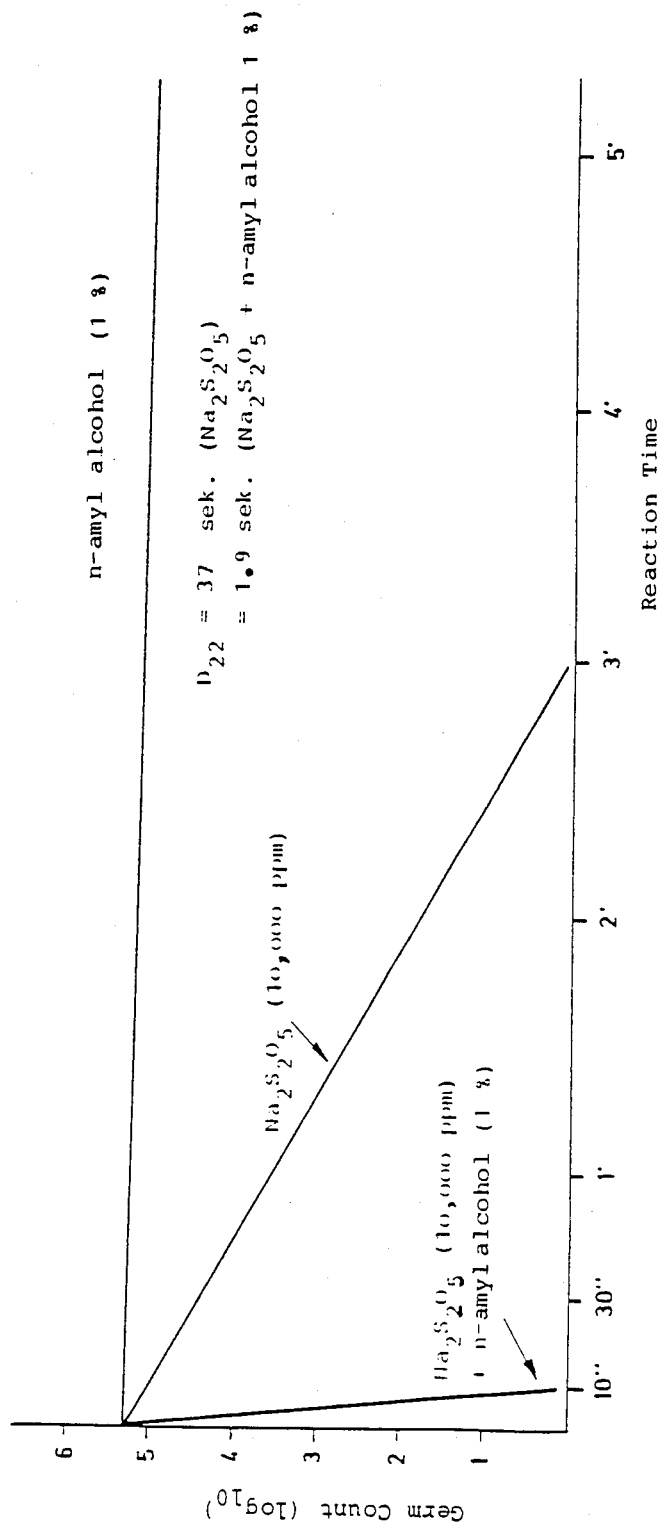

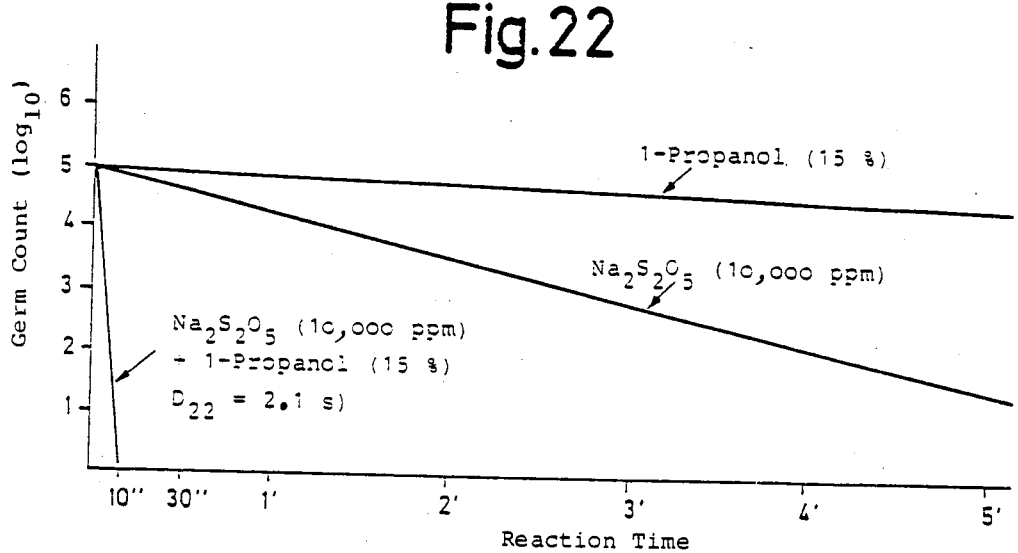
Killing Mucor
Synergistic effect of $Na_2S_2O_5$ (10,000 ppm) and 1-Propanol (15 %) at 22°C
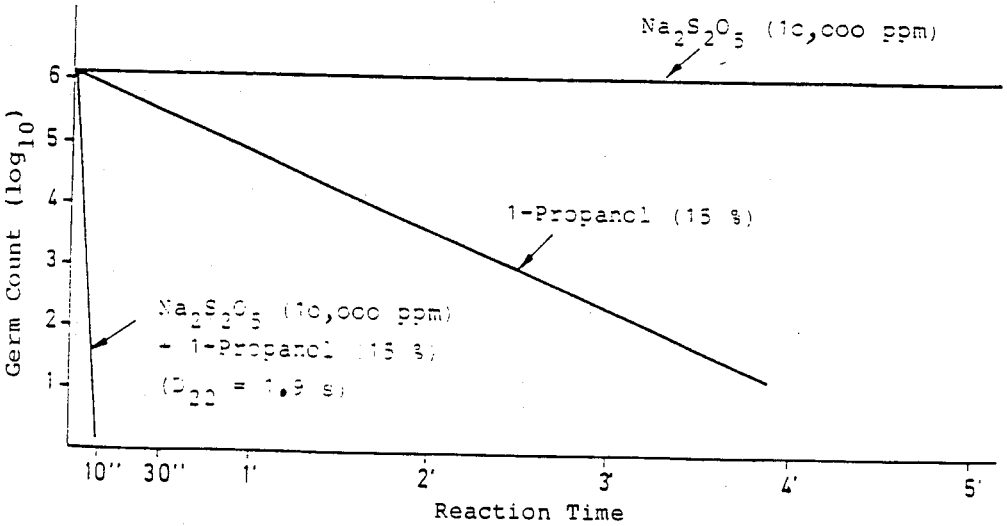
Killing Acetobacters (Gluconobacter)
Synergistic effect of $Na_2S_2O_5$ (10,000 ppm / pH 3.0) and 1-Propanol (15 %) at 22°C Killing Lactic Acid Bacteria (L. dextranicum)
Synergistic effect of $Na_2S_2O_5$ (20,000 ppm / pH 3.0)
and 1-Propanol (10 %) at 22°C

METHOD OF STERILIZING PACKING MATERIALS FOR THE ASEPTIC PACKAGING OF FRUIT JUICE AND WINE

This is a continuation of application Ser. No. 745,337 filed June 17, 1985, now abandoned, the text of which is hereby incorporated by reference.

The invention relates to a method of sterilizing packing materials for the aseptic packaging of fruit juice and wine using sulfurous acid.

Bacterial spores do not develop in fruit juices and wines due to unsuitable conditions for their growth. It is therefore unnecessary to use, for the aseptic packaging of wine, the hydrogen peroxide customary for sterilizing the packaging material, i.e. bottles, bags and containers made of plastic or plastic-coated paper, used for other drinks, such as milk. This could be substituted by sulfurous acid which has already been used to combat the growth of fungi, e.g. during the fermentation and bottling of wines. The effect of sulfurous acid in killing bacteria is, however, too slight to achieve sterility in the short time of a few seconds required by production techniques.

The object underlying the invention is to provide a method of sterilizing packing materials for the aseptic packaging of fruit juice and wine using sulfurous acid which satisfactorily kills germs in a short time.

This object is accomplished in accordance with the invention in that the packing material is treated with aqueous solutions of sulfurous acid and alcohols.

It has been surprisingly found that a mixture of this kind acts synergistically and has a microbicidal effect for the packaging of beverages in question and this effect considerably exceeds that of sulfurous acid without the addition of alcohol.

The following specification serves to explain the invention in more detail in conjunction with two Tables and a number of drawings.

FIGS. 1 to 16 show the effectiveness in killing germs (reducing the number of germs as a function of time) of sulfurous acid and alcohol on their own as well as of mixtures consisting of sulfurous acid and alcohols, when used for various yeasts, fungi and bacteria.

The following microorganisms were used during the course of tests carried out in conjunction with the invention to examine the microbicidal effect of sulfurous acid on its own and sulfurous acid combined with alcohol:

Yeasts (*Saccharomyces cerevisiae*)
Molds (*Aspergillus niger* and Mucor)
Acetobacters (*Acetobacter aceti* and Gluconobacter)
Lactic acid bacteria (*Leuconostoc dextranicum*)

The test substances were aqueous mixtures (solutions) of sodium disulfite ($Na_2S_2O_5$) and ethanol, the ethanol being present in a concentration of between 96 and 100%. Sulfurous acid is most effective in killing germs in a very acid state. The sodium disulfite is therefore, after it has been dissolved in water, acidified with citric acid to a pH of 3.0. The mixed alcohol-containing $Na_2S_2O_5$ solution which has now been acidified contains, apart from alcohol, sulfurous acid in various stages of dissociation, the sulfurous acid being the most effective aseptic substance.

The effectiveness of the substances in killing germs was tested as a function of their concentration at varying temperatures.

FIG. 1 shows the time curve for killing *Saccharomyces cerevisiae* at 22° C. and at various concentrations of $H_2SO_3$ (added in the form of $Na_2S_2O_5$). Killing is quickest at a concentration of 40,000 ppm. A D value of $D_{22}=2$ seconds is hereby reached. (The D value specifies the time in which a predetermined germ count is reduced by one decimal power at a predetermined temperature).

Figure 2:
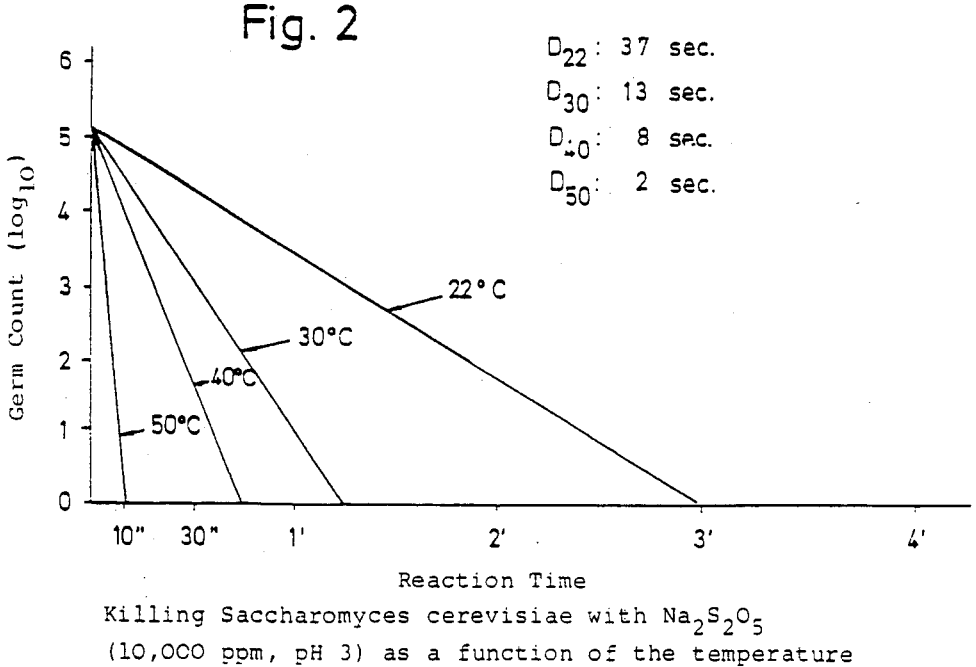

FIG. 2 illustrates the killing of the yeast *S. cervisiae* as a function of the temperature. When the concentration of $Na_2S_2O_5$ remains at 10,000 ppm, the greatest number of germs are killed at 50° C. The decimal reduction time is again approximately 2 seconds ($D_{50}=2$ seconds).

Figure 3:
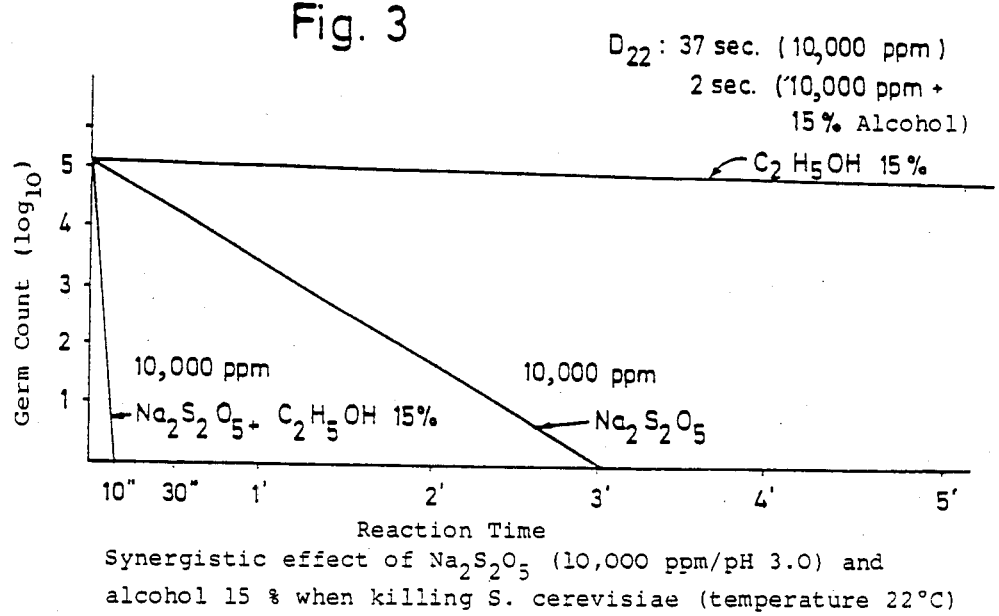

The effectiveness of sulfurous acid in killing germs is precipitously intensified when alcohol (ethanol) is added, as shown in FIG. 3. When sulfurous acid is used alone (10,000 ppm, 22° C.), a D value of $D_{22}=37$ seconds results in the case of *S. cerevisiae* but this may be considerably accelerated by adding ethanol (15% by weight). The D value is then only approximately 2 seconds. As also shown in FIG. 3, cf. the top curve, ethanol on its own has practically no germ-killing effect. The synergistic effect of the mixture used, i.e. sulfurous acid and alcohol, may be clearly read from FIG. 3.

In a comparison with FIGS. 1 and 2, it is seen that exploitation of this synergistic effect no longer necessitates an increase in the concentration of the sulfurous acid to 40,000 ppm (FIG. 1) or increase in temperature to 50° C. (FIG. 2).

Figure 4:
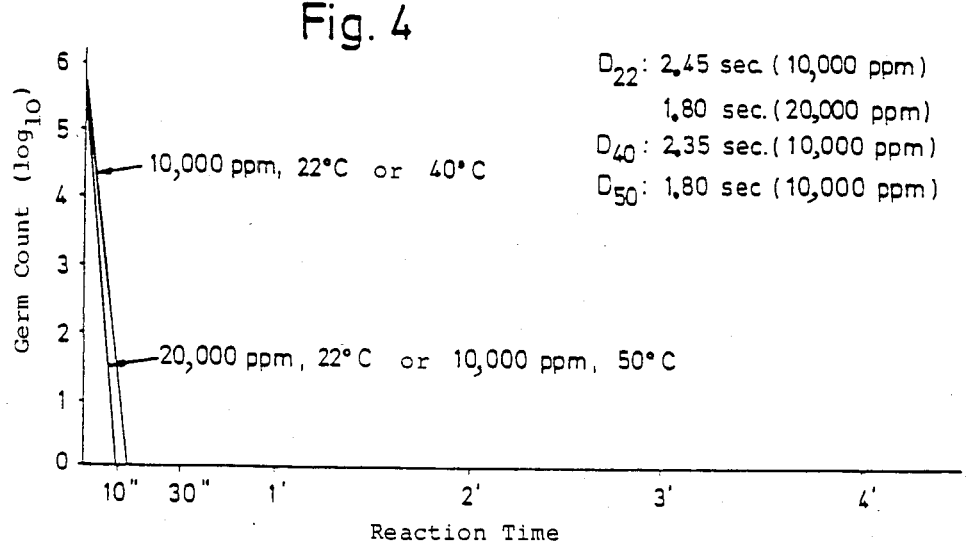

In comparison with yeasts, the conidia of the mold *Aspergillus niger* are easier to kill with sulfurous acid. The concentration of $H_2SO_3$ and the temperature exert only a very slight influence (FIG. 4). A D value of $D_{22}=2.45$ seconds already results at a concentration of only 10,000 ppm at room temperature.

Figure 5:
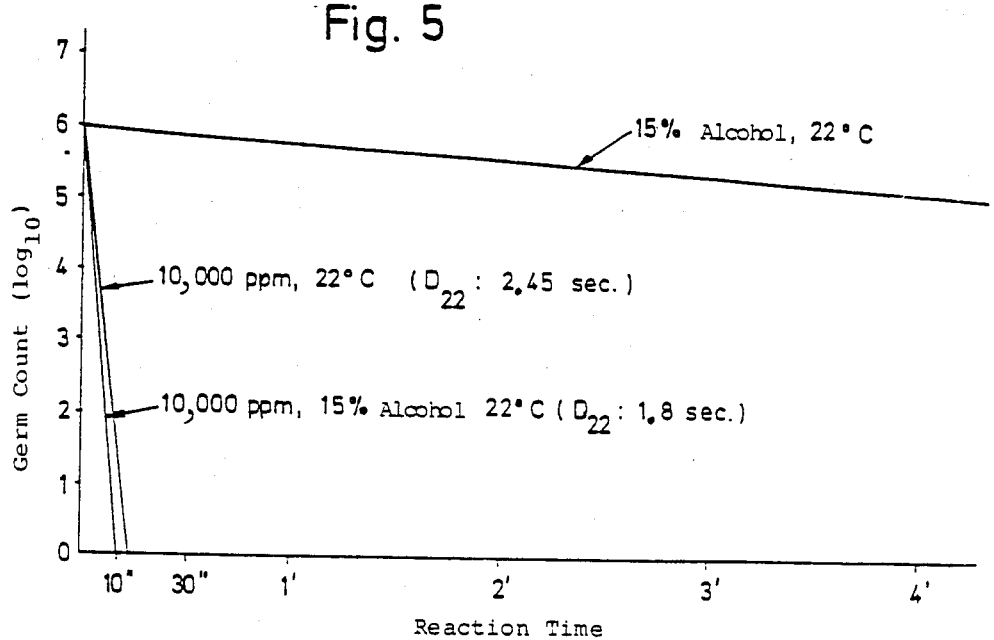

The synergistic effect resulting from a combination of $H_2SO_3$ with alcohol (ethanol) is, at $D_{22}=1.8$ seconds, not very pronounced (FIG. 5).

Figure 6:
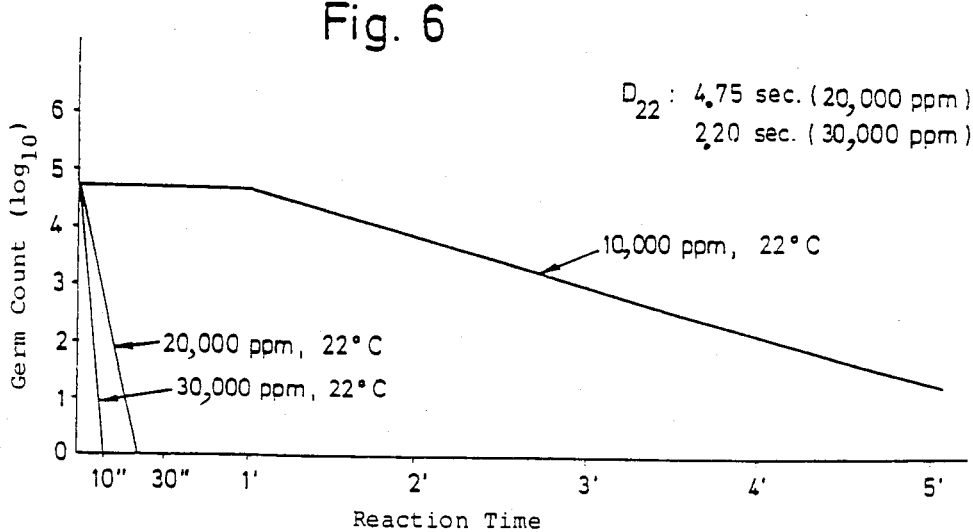
Figure 7:
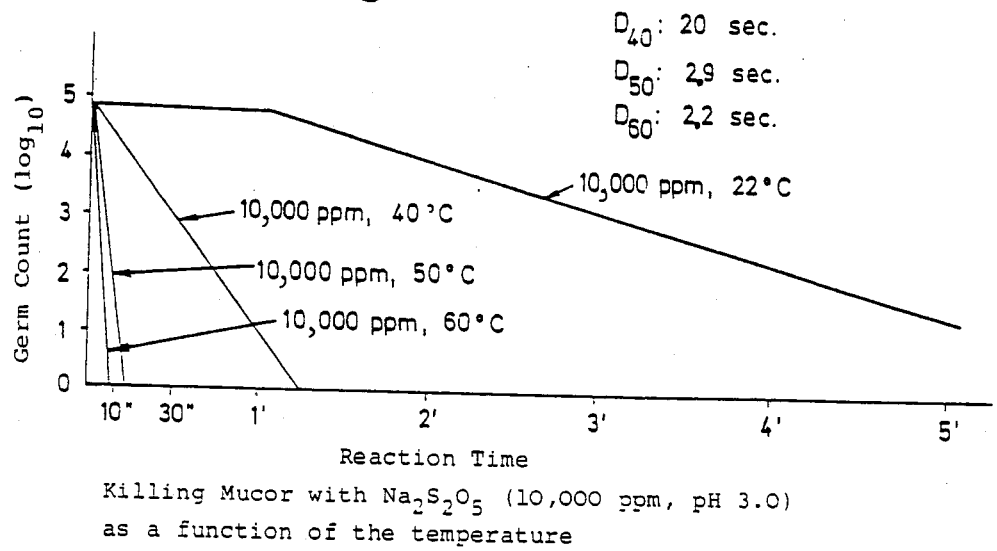

The mold Mucor is more resistant to $H_2SO_3$ than *Aspergillus niger*. The time curves for killing Mucor at different concentrations of $H_2SO_3$ and at different temperatures are shown in FIGS. 6 and 7. A D value in the region of a few seconds is achieved at 30,000 ppm (22° C.) or at 10,000 ppm (60° C.).

Figure 8:
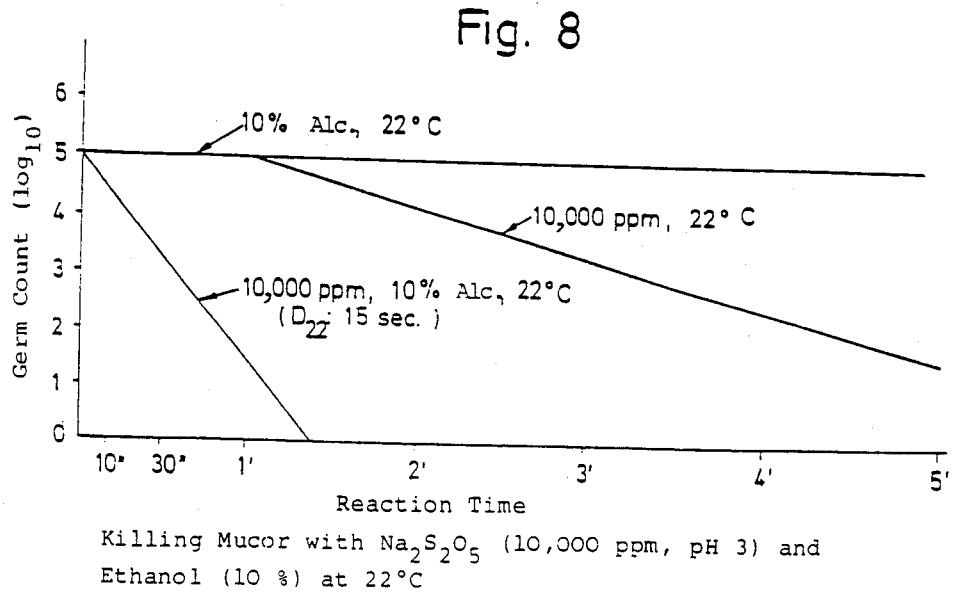
Figure 9:
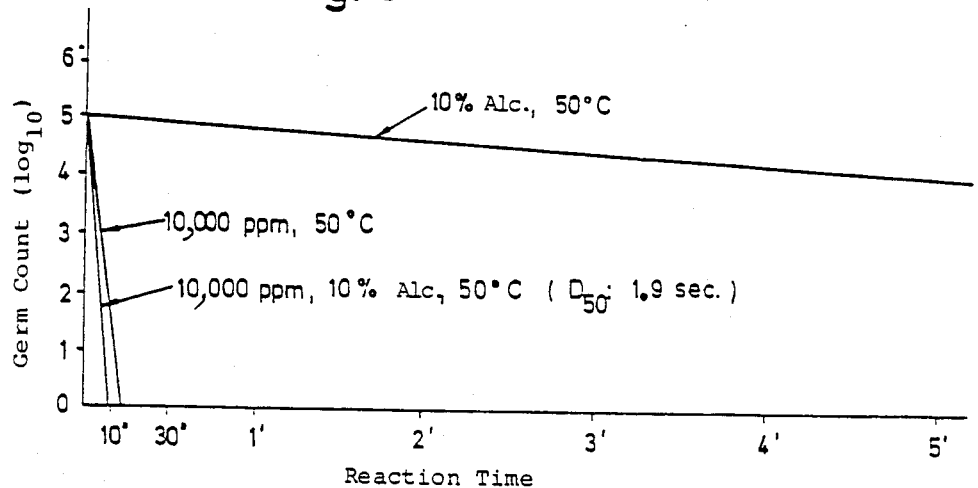

The synergistic effect of a mixture of $H_2SO_3$ and alcohol is also clearly seen in the case of Mucor (FIGS. 8 and 9). The effectiveness of sulfurous acid in killing Mucor is improved by the addition of alcohol both at room temperature (22° C.) and at 50° C.

Figure 10:
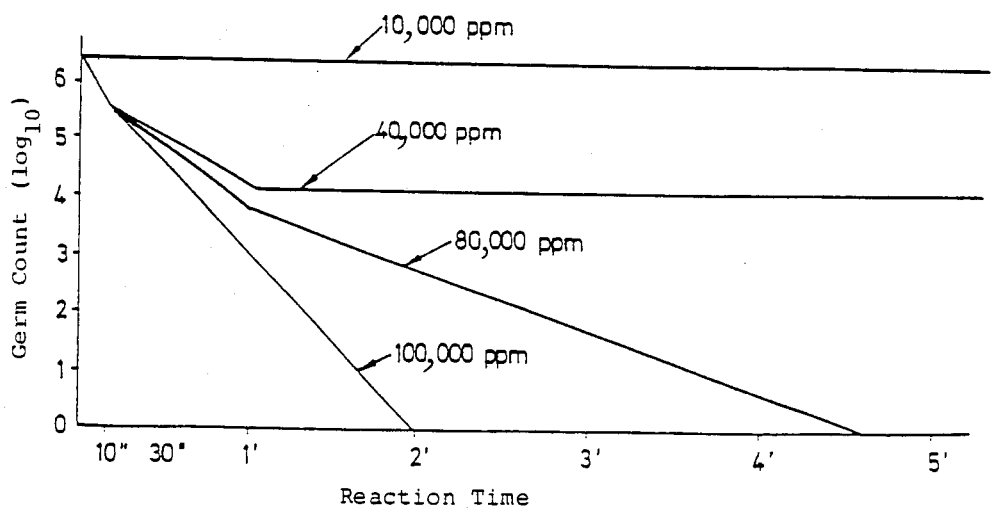
Figure 11:
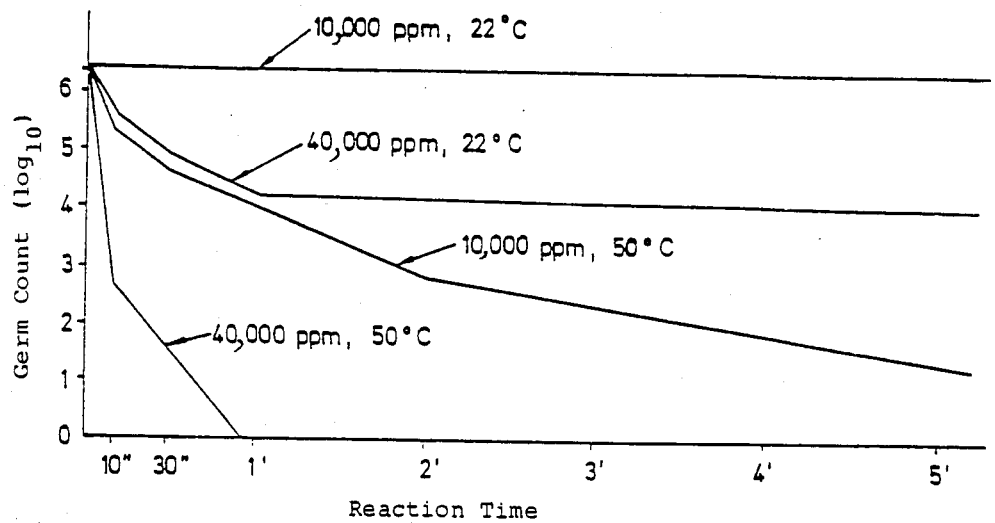

Acetobacters have a quite high resistance to sulfurous acid. As shown in FIGS. 10 and 11, the acetobacter Gluconobacter may be killed only slowly. Neither a high concentration of $H_2SO_3$ nor an increase in temperature are able to bring about any substantial improvement in this respect. A technically exploitable, swift killing of germs with corresponding D values within the range of a few seconds, preferably under 3 seconds, cannot be achieved even with the high concentration of 100,000 ppm at room temperature. The $D_{22}$ value is still 15 seconds.

Figure 12:
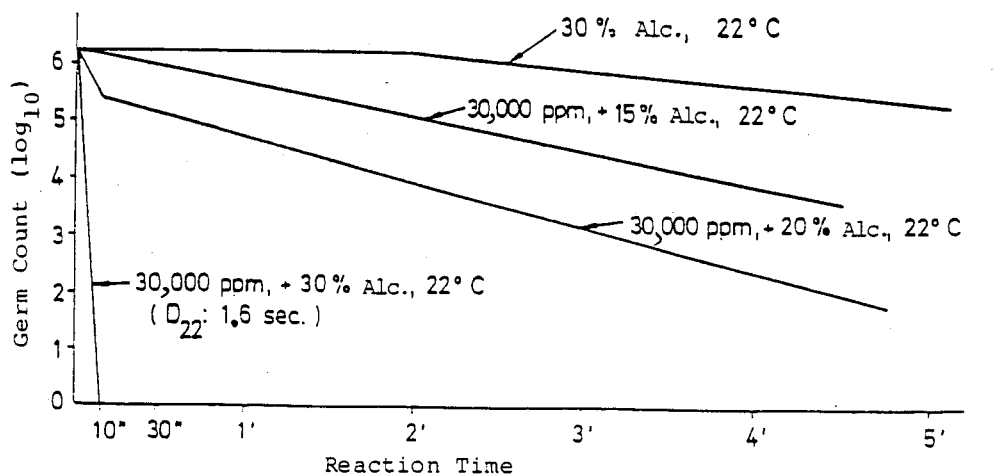

In the case of Gluconobacter, the addition of ethanol to the sulfurous acid proves to be a decisive factor in intensifying the microbicidal effect. A combination of 30,000 ppm $Na_2S_2O_5$ and alcohol (30% by weight ethanol) acts synergistically at room temperature and enables the Gluconobacter to be killed quickly at $D_{22}=$approx. 1.6 seconds (FIG. 12).

Figure 13:
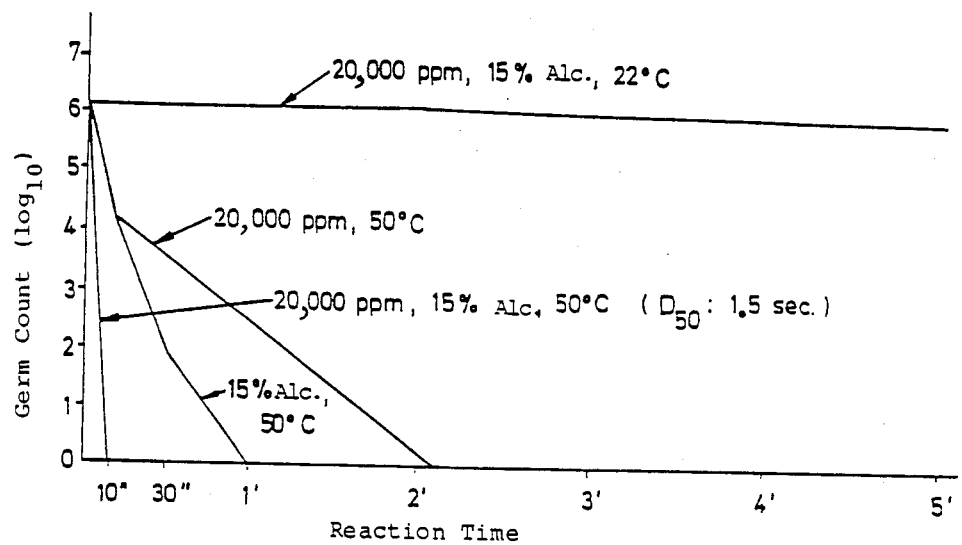

If the temperature is increased to 50° C., a comparable D value ($D_{50} = 1.5$ seconds) may also be achieved with a lower concentration of sulfurous acid (20,000 ppm) and a lower alcohol content (15% by weight) (FIG. 13).

Figure 14:
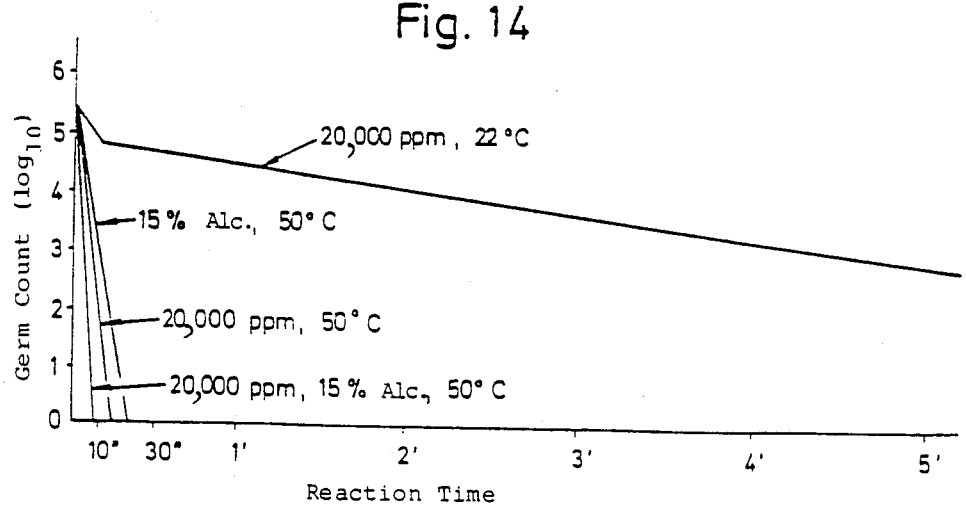

*Acetobacter aceti*, like Gluconobacter, has a high resistance to sulfurous acid. This acetobacter can, however, be killed quickly at a D value of 1.7 seconds due to the synergistic effect of a mixed solution of sulfurous acid and alcohol (20,000 ppm/15% by weight) (FIG. 14).

Figure 15:
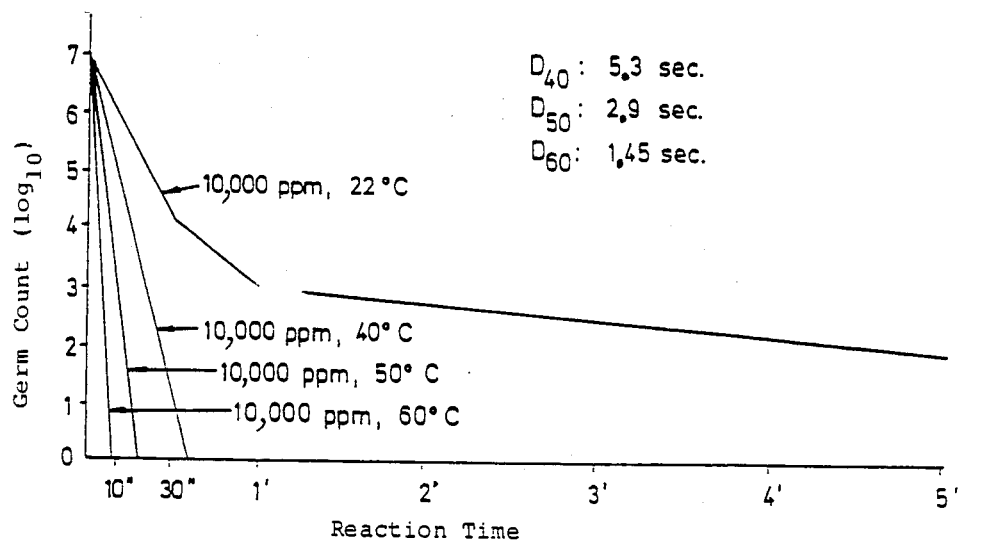

The time taken to kill the lactic acid bacterium *Leuconostoc dextranicum* as a function of the temperature is illustrated in FIG. 15. The greatest number of bacteria are killed at 60° C. at a concentration of 10,000 ppm. The $D_{60}$ value is 1.45 seconds.

Figure 16:
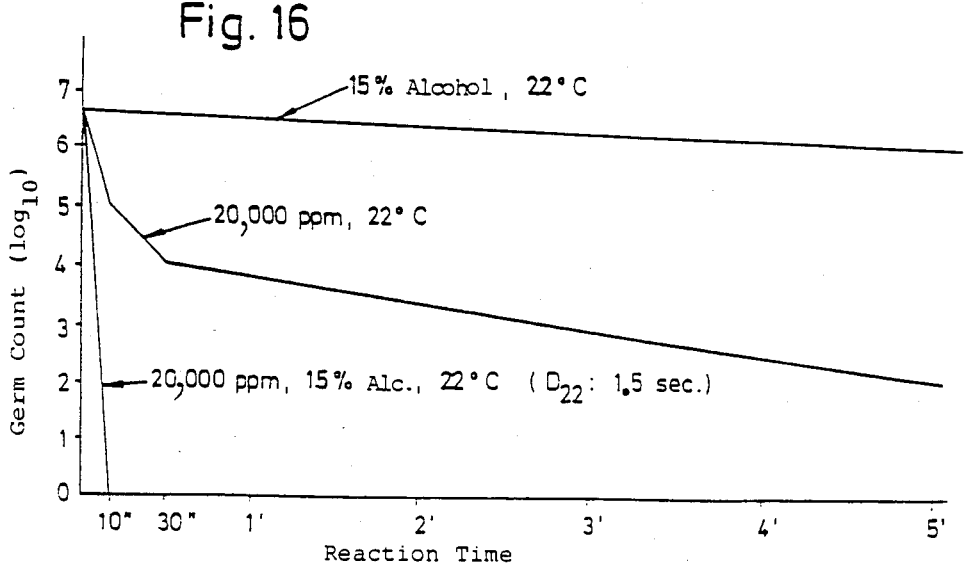

A synergistic effect of the inventive mixture of sulfurous acid and alcohol is also clearly discernible in the case of *L. dextranicum*. FIG. 16 shows that the germ-killing effect of the sulfurous acid (20,000 ppm $Na_2S_2O_5$ at pH 3.0) is considerably intensified by adding ethanol (15% by weight). A D value of $D_{22} = 1.5$ seconds may be achieved.

Figure 17:
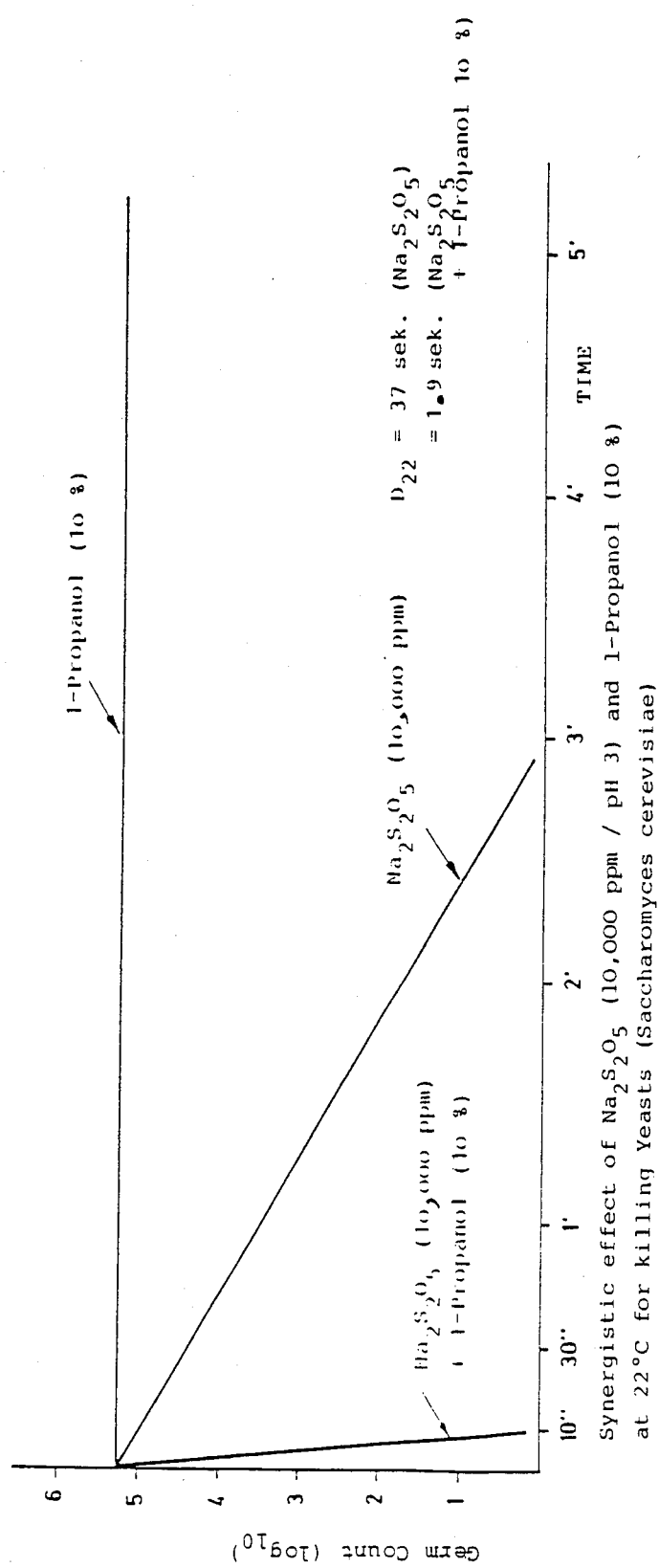
Figure 18:
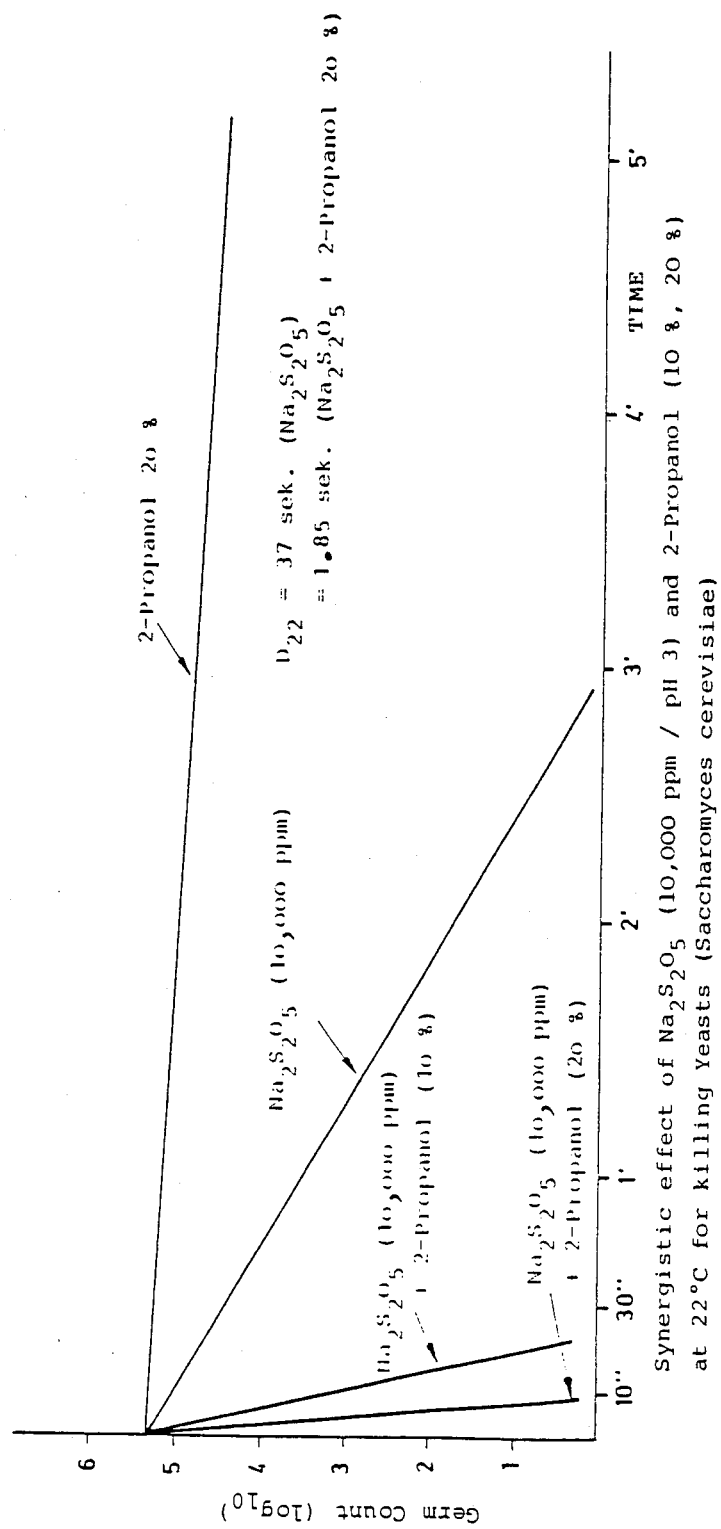
Figure 19:
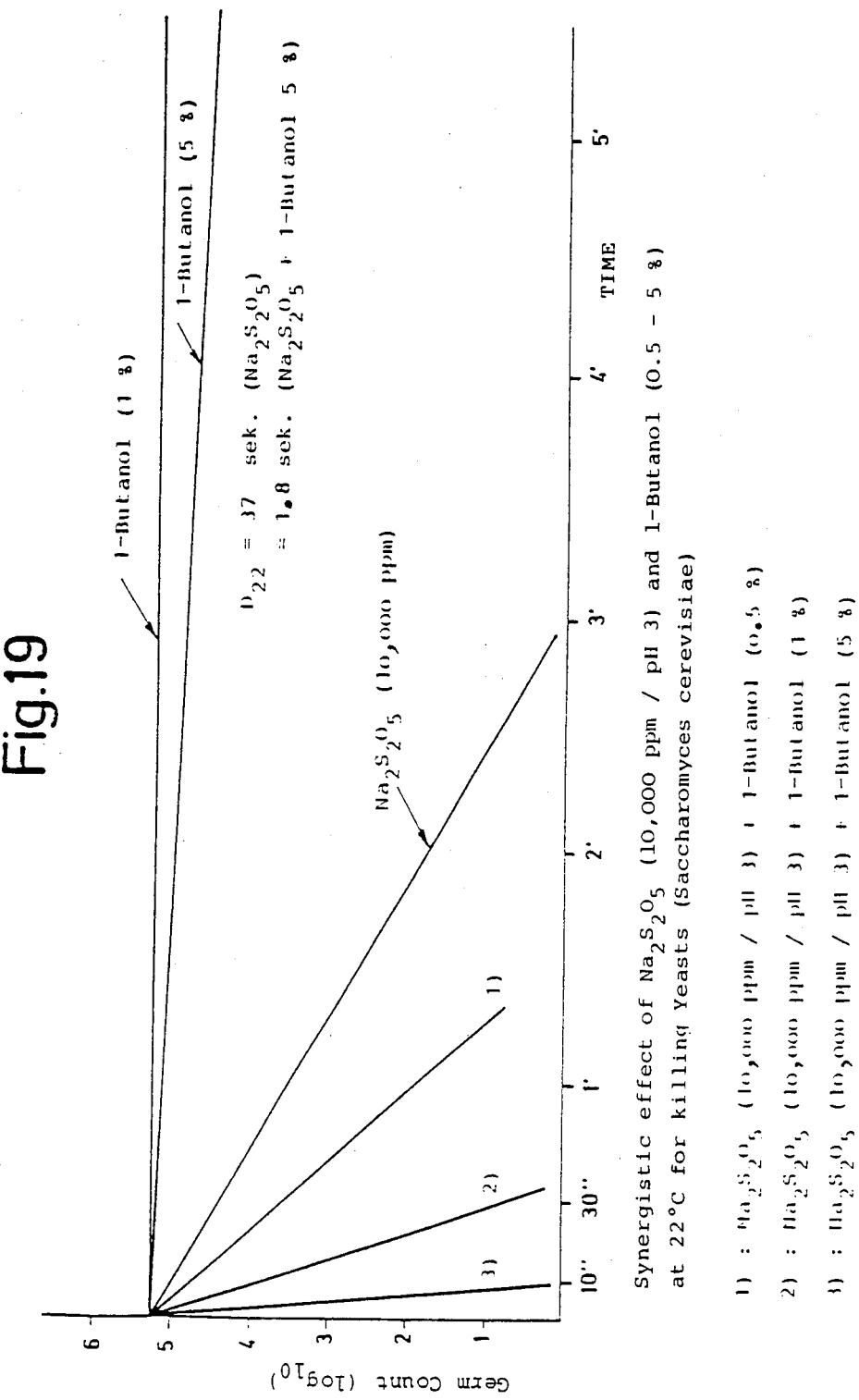
Figure 20:
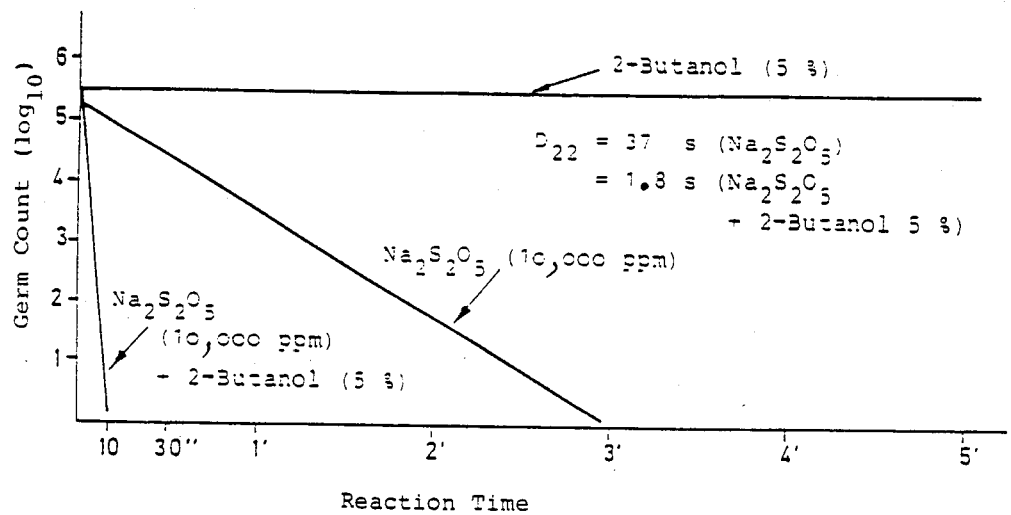
Figure 24:
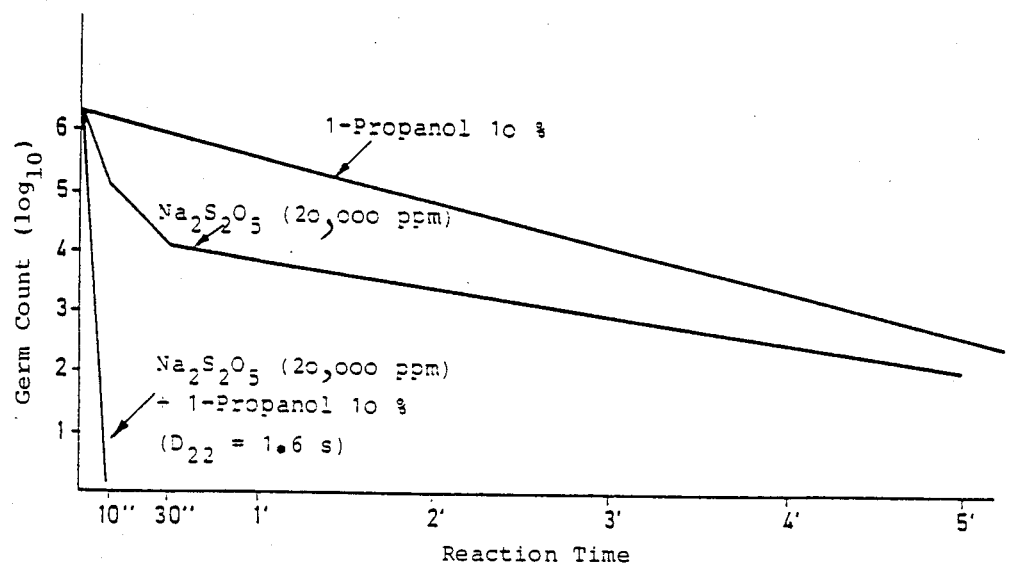

The synergistic effect of the mixture $H_2SO_3$/alcohol is still very apparent when other alcohols are used instead of ethanol. The addition of 1-propanol (FIG. 17), 2-propanol (FIG. 18), 1-butanol (FIG. 19), 2-butanol (FIG. 20) and n-amyl alcohol (FIG. 21) to the sulfurous acid contributes clearly to intensifying the microbicidal effect on yeasts (*Saccharomyces cerevisiae*). The alcohol 1-propanol, in combination with sulfurous acid, accelerates the killing of molds—Mucor—(FIG. 22), acetobacters—Gluconobacter—(FIG. 23) and lactic acid bacteria—*L. dextranicum*—(FIG. 24).

To summarize, it may be ascertained that a synergistic effect of sulfurous acid and alcohol is clearly apparent when killing the germs tested on the basis of the test results described above and illustrated in the Figures. The combination of sulfurous acid and alcohol enables the germs to be killed quickly with D values of between 1 and 2 seconds when the concentration of $H_2SO_3$, the alcohol content and the temperature are selected accordingly. The mixed solution suggested may therefore be used to advantage on a large technical scale, in particular for sterilizing plastic-coated packing materials for the packaging of fruit juice and wine or for sterilizing wine bottles.

The alcohol used is preferably ethanol although it is also possible to make use of other alcohols. The concentration of sulfurous acid is preferably between 10,000 and 100,000 ppm, in particular between 10,000 and 50,000 ppm in relation to the mixture. Particularly favourable concentrations of alcohol are in the range of 10 to 30% by weight, especially 10 to 20% by weight in relation to the mixture. Suitable temperatures for the inventive treatment are between 20° and 80° C., preferably between 20° and 50° C. The sulfurous acid is best obtained by reacting saline sulfur compounds with acid. Apart from $Na_2S_2O_5$, $Na_2SO_3$ is also suitable both alone or in combination with the aforesaid substance. The acid used for adjusting the pH value is preferably citric acid.

The packing material may be treated by dipping, spraying or the like in or with the inventive mixed solution which is synergistically effective. It is also possible to apply the saline sulfur compound, e.g. $Na_2S_2O_5$, from which the sulfurous acid is obtained, to the packing material separately and then to dissolve it by adding an acidified, aqueous alcohol solution.

The results are summarized in the following Tables.

It is particularly favourable to spray the sterilizing mixed solution onto the packing material and then cause it to vaporize due to heating subsequent to its reaction time.

The invention is particularly favourable for use in bottling or packaging wine since wine often contains sulfurous acid and alcohol in any case. This means that no "foreign substances" which could impair the quality of the wine need be used for sterilizing the packing material.

| Killing Grape Pests using Sulfurous Acid in combination with Ethanol | | | | |
|---|---|---|---|---|
| | $Na_2S_2O_5$ | Ethanol | Temp. | D value |
| 1. Yeast (*Saccharomyces cerevisiae*) | 10,000 ppm | 15% | 22° C. | $D_{22} = 2$ sec. |
| 2. Molds (*Aspergillus niger*) | 10,000 ppm | 15% | 22° C. | $D_{22} = 1.8$ sec. |
| 3. Acetobacters (Gluconobacter) | 30,000 ppm | 30% | 22° C. | $D_{22} = 1.6$ sec. |
| | 20,000 ppm | 15% | 50° C. | $D_{50} = 1.5$ sec. |
| (*Acetobacter aceti*) | 20,000 ppm | 15% | 50° C. | $D_{50} = 1.7$ sec. |
| 4. Lactic acid bacteria (*Leuconostoc dextranicum*) | 20,000 ppm | 15% | 22° C. | $D_{22} = 1.5$ sec. |

| Killing Grape Pests using Sulfurous Acid in combination with Alcohols (Propanol, Butanol, Amyl Alcohol) at 22° C. | | | | | | |
|---|---|---|---|---|---|---|
| | $Na_2S_2O_5$ | 1-propanol | 2-propanol | 1-butanol | 2-butanol | n-amyl alcohol | $D_{22}$ Value |
| 1. Yeast (*Saccharomyces cerevisiae*) | 10,000 ppm | 10% | 15% | 5% | 5% | 1% | approx. 2 sec. |
| 2. Molds (Mucor) | 10,000 ppm | 15% | — | — | — | — | approx. 2 sec. |
| 3. Acetobacters (Gluconobacter) | 10,000 ppm | 15% | — | — | — | — | approx. 2 sec. |
| 4. Lactic acid bacteria (*L. dextranicum*) | 20,000 ppm | 10% | — | — | — | — | approx. 2 sec. |

What is claimed is:

1. A method of sterilizing a container for foodstuffs selected from the group consisting of fruit juice and wine which comprises treating said container with an aqueous solution consisting essentially of sulfurous acid and an alcohol, both of which are employed in amounts to provide an aqueous solution effective to reduce at a given temperature the count of yeasts, molds, acetobacters and lactic acid bacteria on said container by one decimal power in a period of not more than 15 seconds.

2. A method in accordance with claim 1 wherein the alcohol is a lower aliphatic alcohol containing from 1 to 5 carbon atoms.

3. A method in accordance with claim 1 wherein the alcohol is 2-propanol.

4. A method in accordance with claim 1 wherein the alcohol is 1-butanol.

5. A method in accordance with claim 1 wherein the alcohol is 2-butanol.

6. A method in accordance with claim 1 wherein the alcohol is n-amyl alcohol.

7. A method in accordance with claim 1 wherein the alcohol is ethanol.

8. A method in accordance with claim 1 wherein the sulfurous acid is present in the aqueous solution in a concentration of from about 1% to 10% by weight of the aqueous solution.

9. A method in accordance with claim 1 wherein the alcohol is present in the aqueous solution in a concentration of from about 10% to 30% by weight of the aqueous solution.

10. A method in accordance with claim 1 wherein the treating of said container is carried out at a temperature of from about 20° to 80° C.

11. A method in accordance with claim 1 wherein the sulfurous acid and alcohol are employed in amounts to provide an aqueous solution effective to reduce at a temperature of about 22° C. the count on said container by one decimal power in a period of not more than 15 seconds.

12. A method in accordance with claim 1 wherein the sulfurous acid is produced in said aqueous solution by reaction of a sulfurous acid-yielding compound with an acid.

13. A method in accordance with claim 1 wherein the sulfurous acid-yielding compound is sodium metabisulfite or sodium sulfite and the acid is citric acid.

* * * * *